United States Patent [19]

Thomas et al.

[11] 4,388,521

[45] Jun. 14, 1983

[54] MODULAR DISINFECTOR DEVICE

[75] Inventors: Michael D. Thomas; Francis E. Ryder, both of Arab, Ala.

[73] Assignee: Ryder International Corporation, Arab, Ala.

[21] Appl. No.: 279,805

[22] Filed: Jul. 2, 1981

[51] Int. Cl.³ .......................... A61L 3/00; A61L 2/04
[52] U.S. Cl. .................................. 219/521; 219/386; 219/401; 422/38; 422/300; 422/301; 422/302; 422/307
[58] Field of Search .............. 422/307, 300, 301, 302, 422/28, 38; 219/386, 401, 521

[56] References Cited

U.S. PATENT DOCUMENTS

| | | | |
|---|---|---|---|
| 3,983,362 | 9/1976 | Hoogesteger et al. | 422/300 X |
| 4,044,226 | 8/1977 | Kadecik et al. | 219/521 |
| 4,158,126 | 6/1979 | Sertz | 422/307 X |
| 4,165,359 | 8/1979 | Thomas et al. | 422/300 X |
| 4,228,136 | 10/1980 | Thomas | 422/307 |
| 4,242,304 | 12/1980 | Ryder | 422/300 X |
| 4,307,288 | 12/1981 | Stine | 422/302 X |
| 4,341,948 | 7/1982 | Sandstrom et al. | 219/521 |

*Primary Examiner*—Barry S. Richman
*Attorney, Agent, or Firm*—Trexler, Bushnell & Wolters, Ltd.

[57] ABSTRACT

Modular lens disinfecting device comprises a plastic housing with a heater and a heat sink lining a portion of the cavity and pressing against opposed caps on a lens case within the housing, thereby transmitting heat to opposed lens cavities within the lens case. A radial flange on the lens case body projects laterally from the housing when the lens case is inserted into the housing, thereby to facilitate manipulation of the lens case upon insertion into or removal from the housing. In making the lens case, the parting plane for the mold that forms the lens case body is positioned so that flash at said plane is precluded from projecting into either of the lens chambers.

12 Claims, 8 Drawing Figures

MODULAR DISINFECTOR DEVICE

BACKGROUND OF THE INVENTION

This invention relates to new and useful improvements in asceptors or disinfectors for contact lenses and like small objects.

Soft contact lenses must be regularly disinfected in order to prevent the wearer of the lenses from becoming infected due to the accumulation of bacteria on the lenses. This disinfecting action generally carried out by heating the lens in a saline solution to a sufficient temperature and for a proper period of time. Many contact lens sterilizers or disinfecting devices operate to disinfect the lenses rather quickly, and in doing so a relatively high temperature is applied to the lenses for a short period of time.

However, it has been found that in subjecting the soft contact lenses to high temperatures, the lenses deteriorate over a period of time, becoming less transparent by taking on a murky or cloudy appearance. It is been found that a preferred disinfecting process is one which is carried out for a somewhat longer period of time and at a lower temperature. Typically, it is preferred that during the disinfecting cycle the range of temperatures to which the lenses are subjected should be in the order of 60° C. to 80° C.

Most contact lens disinfecting units are electrically operated in that they contain electrical heaters which are typically operated from a 115 volt electrical household outlet. Generally speaking devices of this kind are not sufficiently portable to be carried conveniently in a purse or in a coat pocket. Not only does the size of the unit make it impracticle to carry it around in a purse or pocket, but the unit frequently contains a power line cord which simply adds to the bulk of the unit. Pocket-sized contact lens sterilizers are known but many of these embody dual chamber lens cases which are constructed such that the two chambers are completely isolated and reach different temperatures during the disinfecting cycle.

OBJECTS AND SUMMARY OF THE INVENTION

An object of this invention is to provide a modular lens disinfecting device or system for disinfecting contact lenses which reduces the temperature or "heat history" of the contact lenses during the disinfecting cycle so as to prevent the lenses from becoming deteriorated due to exposure to excessive temperatures.

A further object of this invention is to provide a device of the type stated in which the operating temperature of the heating means is limited so as to heat the disinfecting solution in the lens case to within the range of about 60° C. to about 80° C. In accordance with the invention the heating device is thermistor of the type having a resistance that increases as a function of temperature to limit the maximum operating temperature of the heater. Thus, when the maximum operating temperature is reached, a stable condition of the thermistor is present and a "runaway" condition is prevented.

An additional object of this invention is to provide a device of the type stated which is extremely portable and compact while at the same time being easy to use and providing uniform temperature for the solution in the lens case chambers.

A further and more specific object of this invention is to provide a lens case constructed of a molded plastic having a mold parting plane located so that any flash at the parting line will be prevented from projecting into the lens wells. Accordingly, the danger of scratching the lenses from parting line flash is substantially eliminated.

Another important object of this invention is to provide a device of the type stated in which the lens case can be readily removed from the heating chamber and otherwise handled safely while the solution and the body of the case is still hot.

In accordance with the foregoing objects the device comprises a housing having adjacent cavities, a barrier separating said cavities, a generally C-shaped heat sink lining at least part of one of said cavities and including opposed legs and a bight, the bight being presented to the other cavity and forming part of said barrier, electrical heating means in said other cavity and in thermally conductive relation with said bight, said one cavity being open at opposite sides and also open at an end thereof that is opposite to said barrier wall; a lens case having a tubular body forming opposed contact lens-receiving chambers that are in communication, caps removably secured to opposite ends of said body and an annular flange on said body between said caps, said lens case being sized for removable placement in said one cavity such that the caps are in contact respectively with said legs to transfer heat from said heating means to said lens receiving chambers, said annular flange projecting outwardly of said opposite sides to facilitate gripping of said lens case upon removal from and insertion into said one cavity through said open end.

In another aspect of the invention the lens case comprises a tubular body open at its opposite ends, a divider axially intermediate said ends and being an open grid formed by a lattice of intersecting and joined strips of material that divide the body into opposed lens-receiving chambers that communicate with each other and are respectively open at said opposite ends, said body being a one-piece molded plastic member that has a mold parting plane, said plane lying transversely of the longitudinal axis of said body and passing through said joined strips intermediate said chambers such that flash at said plane due to molding is precluded from projecting into either of said chambers.

DETAILED DESCRIPTION

Figure 1:
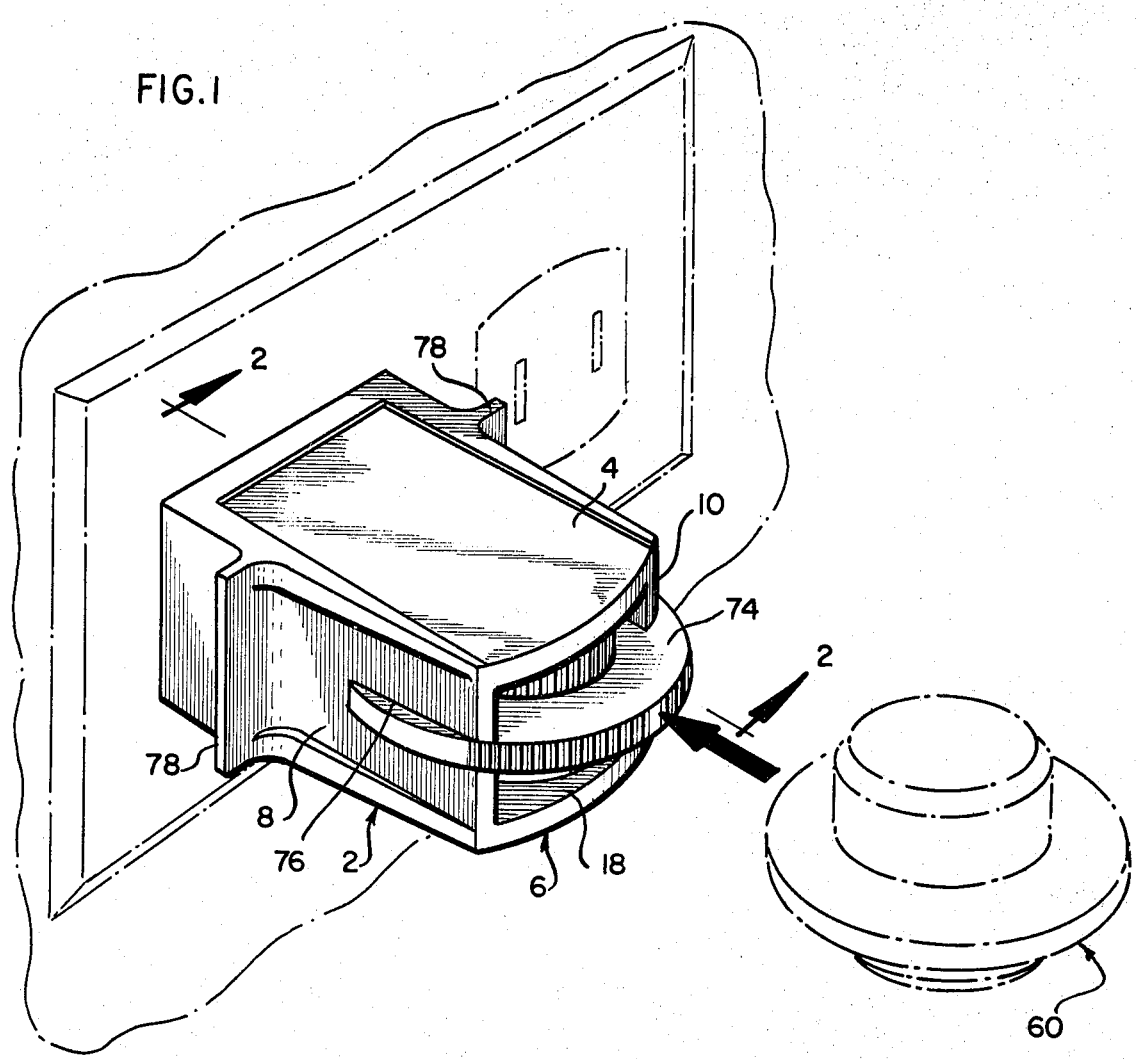
FIG. 1 is a perspective view of a modular lens disinfecting device constructed in accordance and embodying the present invention.

Referring now in more detail to the drawing there is shown a disinfecting device having a plastic housing 2 with a first pair of generally parallel opposed walls 4, 6 and a second pair of generally parallel opposed walls 8, 10 marginally connected to the walls 4, 6. Within a housing 2 is a barrier 12 which cooperates with the walls 4, 6, 8, 10 to define front and rear housing cavities 14, 16, the cavity 16 being somewhat smaller than the cavity 14. The walls 4, 6, 8, 10 also define a front opening 18 and rear opening 20, the rear opening 20 normally being closed off by a back plate 22, the details of which will presently be more fully described.

Positioned within the housing 2 and inset molded therein is a heat sink 24 preferably formed of sheet aluminum or other metal having a high heat conductivity. The heat sink 24 is generally C-shaped and has a bight 26 trapped by the barrier wall 12. The heat sink 24 also has opposed parallel legs 28, 28 which line substantial portions of the walls 4, 6 and are presented to the interior of the cavity 14.

Figure 4:
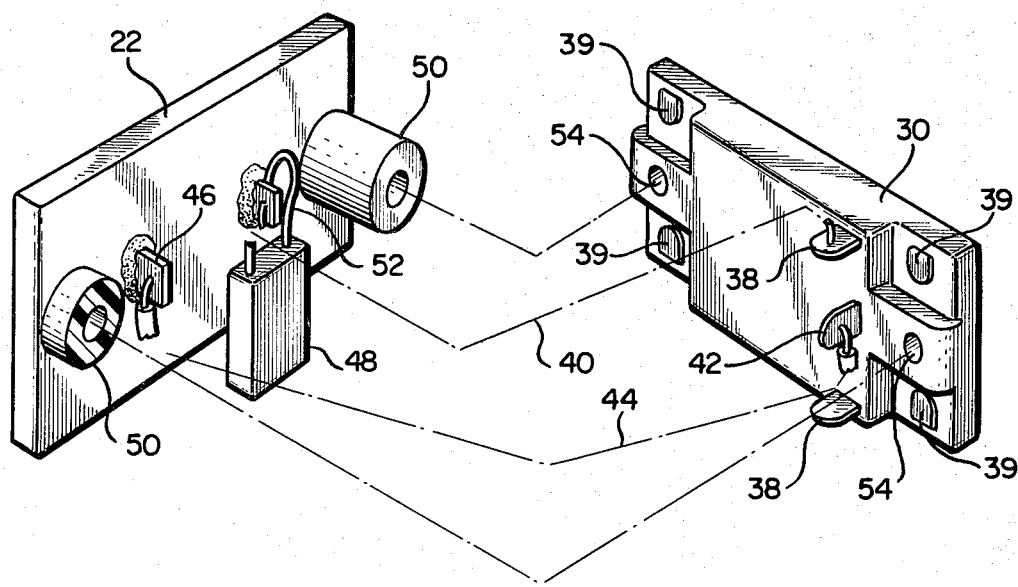
FIG. 4 is a fragmentary exploded perspective view showing portions of the device of FIGS. 1-3.
Figure 2:
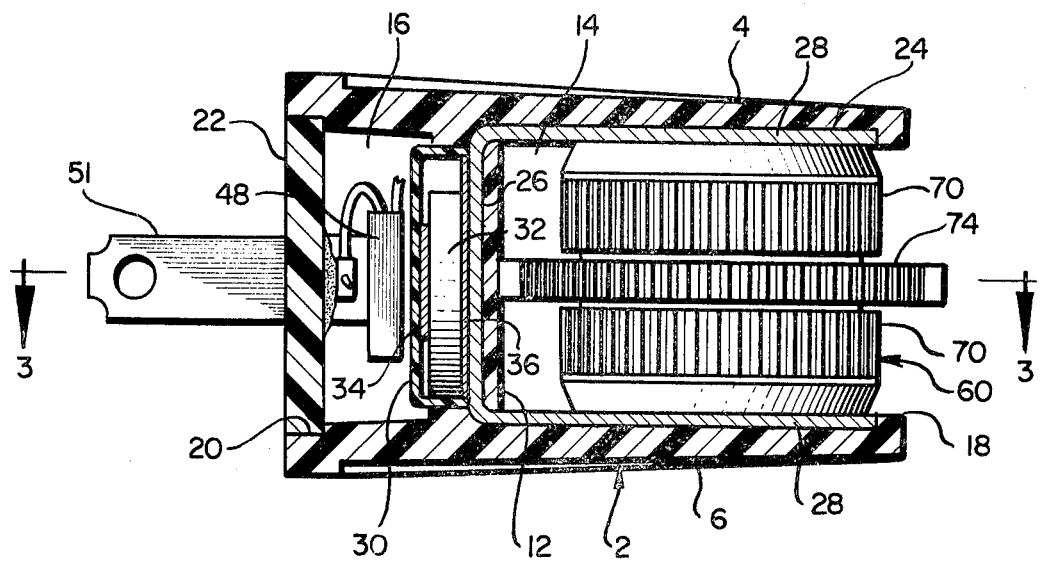
FIG. 2 is a sectional view, on an enlarged scale, taken along line 2—2 of FIG. 1.
Figure 3:
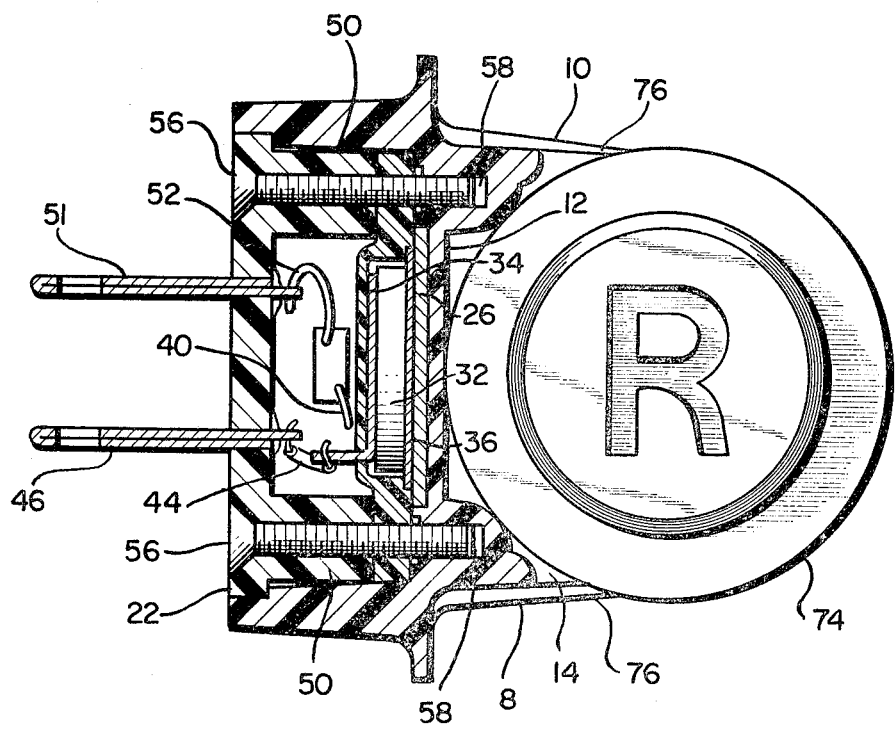
FIG. 3 is a sectional view taken along line 3—3 of FIG. 2.
Figure 5:
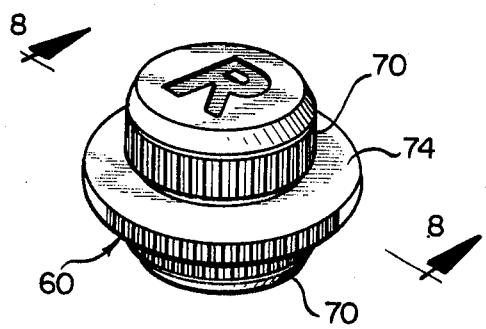
FIG. 5 is a perspective view of the lens case which forms part of the present invention.

Within the cavity 16 is plastic receptacle 30 which receives therein suitable heating means 32 which is preferably a thermistor of the type previously described, namely one in which the resistance increases as temperature increases so as to limit the current flow therethrough and thus the maximum temperature that will be reached by the thermistor. On opposite sides of the thermistor 32 are metallic contact plates 34, 36, the contact 36 pressing against the bight 26 and the thermistor 32 so that heat from the thermistor is conducted to the heat sink through the plate 36. As best seen in FIGS. 2, 3, and 4 the contact plate 36 forms a closure for the receptacle 30. The contact plate 36 has bendable tabs 39 (FIG. 4) that project through the receptacle 30 and are bent to hold the plate and receptacle assembled. The plate 36 also has a pair of terminal tabs 38, 38 (FIG. 4) at which a wire 40 may be selectively connected. Likewise, the contact plate 34 has a tab 42 projecting through the receptacle 30 for connection with a wire 44. The wire 44 is in turn connected to a metallic electrical terminal 46. The wire 40 is electrically connected to a fuse link 48 which is in turn connected by wire 52 to electrical terminal 51. The contact plates 34, 36 are respectively electrically connected to opposite terminals of the thermistor 32. There is thus provided an electrical circuit from the terminals 46, 51 through the thermistor 32. The terminals 46, 51 are of the type designed for plug-in connection to a conventional household electrical outlet as best shown in broken lines in FIG. 1.

As best seen in FIGS. 3 and 4 the terminals 46, 51 project rearwardly through the back plate 22, the latter having internal spacer bosses 50, 50. These bosses have axial bores which are aligned with companion holes 54, 54 (FIG. 4) for receiving screws 56, 56. The screws 56, 56 are threaded into threaded holes 58, 58 that are formed in thickened portions at the opposite ends of the barrier 12. Removal of the screws 56 permits removal of the end plate 22 and the receptacle 30 and components therein.

Figure 6:
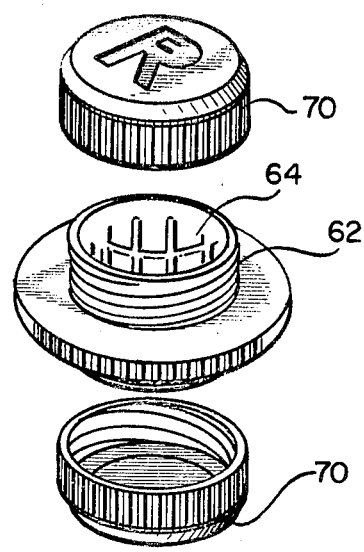
FIG. 6 is an exploded perspective view of the lens case.
Figure 7:
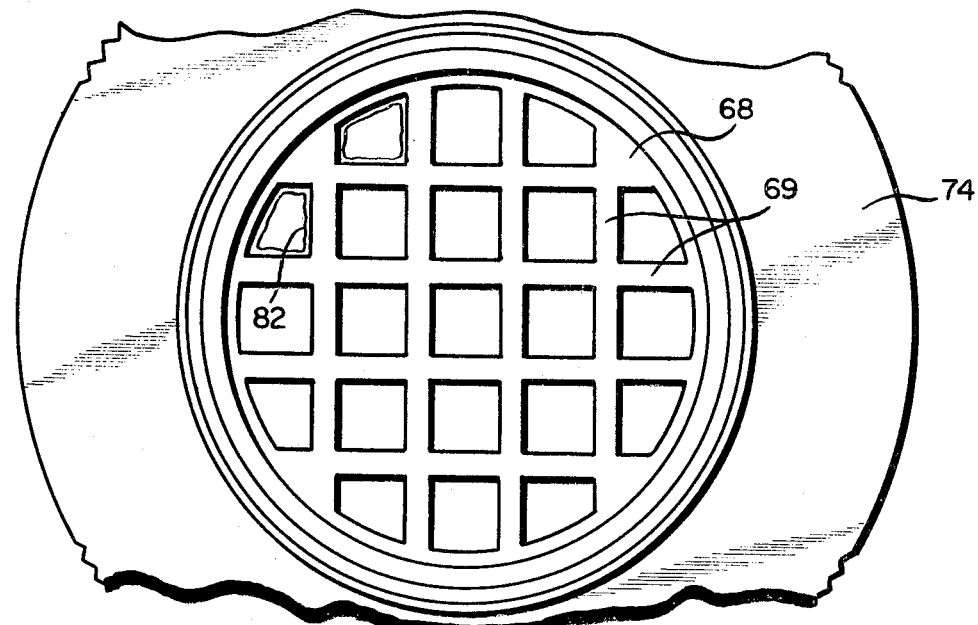
FIG. 7 is a fragmentary top plan view, on an enlarged scale, of the lens case.
Figure 8:
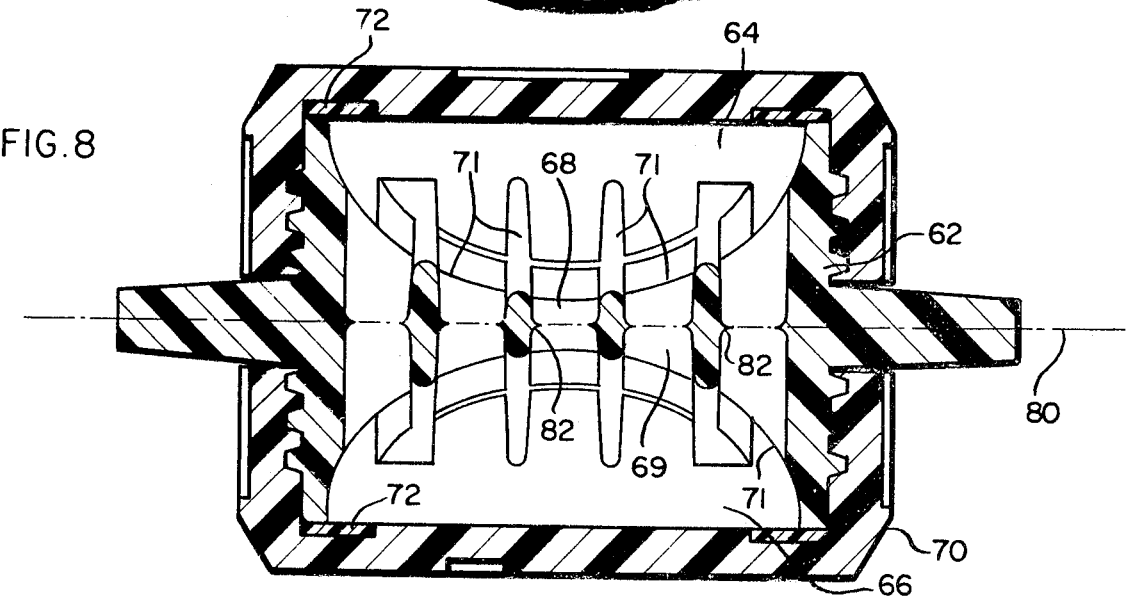
FIG. 8 is a sectional view, on an enlarged scale, taken along line 8—8 of FIG. 5.

Provided for cooperation with the housing 2 is a plastic lens case 60 having a tubular body 62 that is a one-piece molded plastic member. The tubular body 62 is formed with opposed chambers or wells 64, 66 which are in communication with each other rather than being isolated. The chambers are separated by a divider which is formed of a lattice 68 of intersecting and joined strips 69 of material that constitute an open grid-like structure. As best seen in FIGS. 6 and 8 the grid is contoured to form substantially an arcuate shape for the proximate or adjacent ends of the chambers 64, 66. Thus, as best seen in FIG. 8, the strips 69 will increase in axial length from near the central axis of the tubular member 62 toward the radial outermost part of each chamber 64, 66 and will have arcuate edges 71.

Exteriorly thereof, the opposite open ends of the tubular body 62 are externally threaded to receive closure caps 70, 70 which are marked "L" and "R" for identifying, when the device is in use the chamber containing the right or left lens. An annular sealing gasket 72 is formed on each end cap 70 for sealing against the rim of the tubular body, as seen in FIG. 8. Also formed on the body 62 is an annular radially outwardly extending flange 74. This flange is positioned between the caps 70, 70 when the latter are mounted on the tubular body 62.

In the disinfecting cycle suitable solution is placed within the chambers 64, 66 together with the lenses therein. The lens case with the caps thereon is inserted into the housing 2 through the front opening 18 until the caps 70 are completely within the cavity 14. The distance between the legs 28, 28 is preferably slightly less than the distance between the flat end surfaces of the caps 70, 70 and the walls 4, 6 have a modicum of resiliency. Consequently, there is slight pressure exerted on the caps 70, 70 by the legs 28, 28, thereby insuring efficient conduction of heat to the lens wells 64, 66. The walls 8, 10 are formed with slots 76, 76 extending rearwardly from the front opening 18 for purposes of receiving the lens case flange 74 that projects through the slots 76, 76. Thus, the flange 74 may be gripped on opposite sides of the housing 2 to remove readily a hot lens case from within the housing 2 upon completion of a disinfecting cycle. Furthermore, the housing is formed with lateral flanges 78, 78 which facilitate gripping the housing itself, particularly when the latter is hot.

An important feature of the invention lies in the molding of the tubular body 62. As best shown in FIG. 8 the body 62 has a mold parting plane 80 (where the mold members for molding the body 62 meet) which is perpendicular to the longitudinal axis of the body 62 and passes centrally through the flange 74. This parting plane 80 also passes through the various strips 69 of the lattice 68 between opposite edges 71 with the result that plastic flash such as at 82 (shown exaggerated for illustration) is precluded from projecting into either chamber 64 or 66. As a result, the flash 82 will not contact and possibly scratch soft contact lenses within the chamber 64, 66. Rather the lenses will engage the rounded surfaces 71 of the joined strips of the lattice to provide smooth surface portions against which the lenses abut.

During molding the surfaces 71 provided by the lattice structure 68, as well as any other surfaces against which the lenses will engage will be formed by machined surfaces of the mold member that are disposed away or spaced from the parting line of the mold components (corresponding to plane 80). As such any flash 82 produced, will not be in the critical area of these lens supporting or engaging surfaces. Thus, with this aspect of the invention, it is assured that all surfaces 71 against which the lenses will rest are free of flash or any other sharp protuberances which might damage the lenses or any coatings thereon.

While a preferred embodiment of the present invention has been illustrated and described, it is envisioned that those skilled in the art once apprised of said invention may devise various modification without departing from the true spirit and scope of the invention as defined in the claims appended hereto.

The invention is claimed as follows:

1. Modular lens disinfecting device comprising a plastic housing having front and rear ends and a cavity with a first pair of opposed walls, a metal heat sink lining said opposed walls and being presented toward said cavity, a second pair of opposed walls transverse to said first pair of walls and cooperating therewith to define a front opening into said cavity, said second pair of walls having slots extending from said opening toward said rear end to form additional openings into said cavity, electrically operating heating means in thermal relation with said heat sink, and a plastic lens case sized for removable insertion into said cavity through said front opening, said case having opposed surfaces engaging said heat sink and radial flange means projecting through said slots.

2. Device according to claim 1 in which said heating means is portioned between said front and rear ends outside of said cavity, and a part of said lens case projects outwardly of said front opening.

3. Modular lens disinfecting device comprising a housing having adjacent cavities, a barrier separating said cavities, a generally C-shaped heat sink lining at least part of one of said cavities and including opposed legs and a bight, the bight being presented to the other cavity and forming part of said barrier, electrical heating means in said other cavity and in thermally conductive relation with said bight, said one cavity being open at opposite sides and also open at an end thereof that is opposite to said barrier wall; a lens case having a tubular body forming opposed contact lens-receiving chambers that are in communication, caps removably secured to opposite ends of said body and an annular flange on said body between said caps, said lens case being sized for removable placement in said one cavity such that the caps are in contact respectively with said legs to transfer heat from said heating means to said lens-receiving chambers, said annular flange projecting outwardly of said opposite sides to facilitate gripping of said lens upon removal from and insertion into said one cavity through said open end.

4. Device according to claim 3 in which said caps have flat end walls against which said legs are respectively in pressure engagement, said housing having a closure for said other cavity that is opposite to said barrier, electrical terminals projecting through said closure and in circuit-forming relationship with said heating means, and outward projecting heat-dissipating elements on said housing forming finger grippers for manipulating said housing.

5. A modular contact lens disinfector device for use with a compatibly shaped lens case, said device comprising: a housing having adjacent cavities, barrier means separating said cavities, a first one of said cavities having an open end and at least two opposed wall portions with said lens case disposable in said first cavity through said open end; a heat sink including a pair of opposed elongate legs extending substantially parallel and connected by a bight section, said opposed legs being disposed in said first cavity and providing a lining for at least a portion of the opposed walls of said first cavity, the bight section of said heat sink being disposed in the other of said cavities and forming at least a part of said barrier means; electrical heating means housed in said other cavity in thermally conductive relation with said bight section; said first cavity including the opposed legs of said heat sink having the open end thereof disposed opposite to said barrier means, and being sized such that said compatibly shaped lens case may be removably placed in said first cavity with the upper and lower surface portions thereof in sliding contact respectively with the opposed legs of said heat sink so that heat may be transferred from said electrical heating means to said heat sink, and from said heat sink to said lens case.

6. A device according to claim 5 wherein said one cavity further includes a second pair of opposed side walls that are not lined by said heat sink, said second pair of side walls having slots formed therein, such that said cavity can accommodate a lens case having a substantial annular flange portion designed to be disposed in said slots and to extend exteriorally of said cavity to facilitate gripping of the lens case upon removal from and insertion into said cavity.

7. A device according to claim 5 or 6, wherein said housing includes a closure for said other cavity that is disposed opposite said barrier, electrical terminal means projecting through said closure and in circuit forming relationship with said heating means, said terminal means including a pair of prong terminals of the type adapted for engagement in a conventional outlet socket.

8. A device according to claim 7, wherein said housing further includes outwardly projecting heat dissipating elements on a side thereof, which elements also serve to form finger grippers for manipulating the housing to and from engagement with said outlet socket.

9. A modular lens disinfecting device including a housing defining adjacent cavities, barrier means separating said cavities, a generally C-shaped heat sink lining at least part of one of said cavities and including the opposed parallel leg portions, and a bight portion, the bight portion being presented to the other cavity and forming part of said barrier, electrical heating means disposed in said other cavity, and in thermally conductive relation with said bight portion, said one cavity being open at an end opposite said barrier wall, closure means for said other cavity dispose oppositely of said barrier wall, and electrical terminal means in the form of conventional prong type terminals adapted for disposition in a conventional outlet socket and projecting through said closure and in circuit forming relationship with said heating means; a lens case disposable in said one cavity, and including a tubular body having opposed contact lens receiving chambers, removable cap means secured to opposite ends of said body for closing said chambers, said lens case being sized for removable placement in said one cavity such that the caps thereof will be in heat conductive contact respectively with said legs to transfer heat from said heating means to said lens receiving chambers.

10. The combination according to claim 9, wherein said one cavity includes opposed side walls having slots formed therein, which slots open to the open end of said cavity, said lens case having an annular flange oriented transversely to the axis of said tubular body, such that upon disposition of said lens case in said cavity, said annular flange will be engaged in said slots in the opposed side walls, and will project outwardly of said opposed walls to facilitate gripping of the lens case upon removal from and insertion into the open end of said cavity.

11. The combination according to claim 9, wherein said lens case includes means dividing said chambers, which dividing means is defined by a lattice structure providing communication between the respective lens receiving chambers.

12. The combination according to claim 11, wherein said lattice structure is defined by an open grid comprised of intersecting strips of material that divide the body into opposed lens receiving chambers, said body and said lattice structure being of a one-piece molded plastic construction including a parting plane, said plane lying transversely of the longitudinal axis of said tubular body and passing through said joined strips which define said lattice and disposed at a location intermediate said chambers, such that any flash that may occur at said plane during the molding operation is precluded from projecting into either of said chambers.

* * * * *